United States Patent
Schmidt et al.

(10) Patent No.: US 9,903,770 B2
(45) Date of Patent: Feb. 27, 2018

(54) THERMAL CONDUCTIVITY DETECTOR CIRCUIT AND METHOD FOR OPERATING THE SAME

(71) Applicant: Siemens Aktiengesellschaft, Munich (DE)

(72) Inventors: Glen Eugene Schmidt, Bartlesville, OK (US); Udo Gellert, Bellheim (DE); Aosheng Wang, Eden Prairie, MN (US)

(73) Assignee: Siemens Aktiengesellschaft, Munich (DE)

( * ) Notice: Subject to any disclaimer, the term of this patent is extended or adjusted under 35 U.S.C. 154(b) by 364 days.

(21) Appl. No.: 14/669,981

(22) Filed: Mar. 26, 2015

(65) Prior Publication Data

US 2015/0292960 A1    Oct. 15, 2015

(30) Foreign Application Priority Data

Apr. 14, 2014    (EP) .................... 14164552

(51) Int. Cl.
| | |
|---|---|
| *G01K 17/00* | (2006.01) |
| *G01N 25/18* | (2006.01) |
| *G01N 30/66* | (2006.01) |
| *G01N 30/86* | (2006.01) |

(52) U.S. Cl.
CPC ............. *G01K 17/00* (2013.01); *G01N 25/18* (2013.01); *G01N 30/66* (2013.01); *G01N 30/8641* (2013.01)

(58) Field of Classification Search
CPC ........ G01N 25/18; G01N 25/72; G01N 25/12; G01N 30/66; G01N 30/8641; G01N 30/62; G01N 30/86; G01K 17/00; G01K 17/04; G01K 17/06; G01K 13/00; G01K 13/02

See application file for complete search history.

(56) References Cited

U.S. PATENT DOCUMENTS

| | | |
|---|---|---|
| 3,714,591 A | 1/1973 | Allington |
| 5,756,878 A | 5/1998 | Muto et al. |
| 2008/0291966 A1 | 11/2008 | Engel et al. |

FOREIGN PATENT DOCUMENTS

| | | |
|---|---|---|
| DE | 43 10 384 A1 | 10/1994 |
| GB | 1 557 968 A | 12/1979 |
| WO | WO 2012/021681 A2 | 2/2012 |

*Primary Examiner* — Nikolay Yushin
(74) *Attorney, Agent, or Firm* — Cozen O'Connor

(57) ABSTRACT

A thermal conductivity detector includes a switch controllable to short-circuit the input of an amplifier to improve the thermal conductivity detector for use in gas chromatography without the need of an additional reference cell, wherein a digital signal processor calculates a transfer function of an analog signal processor from a digitized difference signal received in response to short-circuiting the input of the amplifier at a given time when solely a reference carrier fluid passes through a measuring cell, and the digital signal processor recovers a detector signal by deconvoluting the digitized difference signal with a transfer function.

3 Claims, 1 Drawing Sheet

THERMAL CONDUCTIVITY DETECTOR CIRCUIT AND METHOD FOR OPERATING THE SAME

BACKGROUND OF THE INVENTION

1. Field of the Invention

The present invention relates to a thermal conductivity detector and a method for operating the same.

2. Description of the Related Art

Thermal conductivity detectors are used to detect certain liquid or gaseous substances (fluids) based on their characteristic thermal conductivity, particularly in gas chromatography. Here, components or substances of a gas mixture are separated by passing a sample of the gas mixture in a carrier gas (mobile phase) through a separation column containing a stationary phase. The different components interact with the stationary phase that causes each component to elute at a different time, known as the retention time of the component. The separated substances are detected by a thermal conductivity detector that includes has a measuring cell with an appropriate detector element, e.g., an electrically heated filament disposed in a measurement channel. Depending on the thermal conductivity of the substance flowing past the heated filament, more or less heat is diverted from the heating filament to the wall of the measurement channel, and the heating filament is correspondingly cooled to a greater or lesser degree. As a result of the cooling of the heating filament, its electrical resistance changes, which is detected.

For this purpose, the heating filament may be disposed in a measuring bridge, which contains additional resistors and an additional heating filament in a reference channel through which a reference fluid flows (e.g. U.S. Pat. No. 5,756,878, FIG. 8). The thermal conductivity of the substance passing the heating filament is obtained from an amount of energy which is supplied to the measuring bridge and is controlled to maintain the temperature of the heating filament at a predetermined temperature. Instead of the resistors, further filaments may be provided which are fluidically parallel or in series with the filaments in the measurement channel and the reference channel, respectively.

From FIG. 2 of US 2008/0291966 A1, e.g., a thermal conductivity detector is known that includes a measuring cell as well as a reference cell. The measuring cell is passed through by the carrier gas stream whereas the reference cell is passed solely by the carrier gas. The detector signals provided by the respective thermal conductivity detector elements of the measuring and reference cells are amplified and then subtracted from each other to obtain a difference signal that is only representative of the sample. For further digital processing, the difference signal must be digitized with a high resolution of, e.g., 24 bits which corresponds to a dynamic range of 144 dB. Thus, noise and drift characteristics of the difference signal are very important.

A problem with the additional reference cell is that it may have noise, drift and physical response characteristics that do not exactly match or track those of the measuring cell. These characteristics work against the quality of the detector signal from the measuring cell because they may introduce degradation in the difference signal when the reference signal is subtracted from the detector signal.

Additionally, chromatography applications can sometimes be limited by the number of reference cells available for measurement. Groups of detector cells are often assigned to one fixed reference cell. Thus, the ability to use any detector without a reference constraint would allow for far greater freedom to application chemist and would also reduce complexity and costs.

SUMMARY OF THE INVENTION

It is therefore an object of the present invention to provide a thermal conductivity detector for use in gas chromatography without the need for an additional reference cell.

It is a further object of the present invention to provide a method for operating a thermal conductivity detector without the need for the additional reference cell.

These and other objects and advantages are achieved in accordance with the invention by providing a method and thermal conductivity detector comprising a measuring cell to be passed through by a sample fluid in a reference carrier fluid stream, where the measuring cell contains at least one thermal conductivity detector element and providing a detector signal, an analog signal processor including an amplifier for amplifying the detector signal, a low-pass filter for providing a running average of the amplified detector signal, and a subtractor for generating a difference signal from the amplified detector signal and the running average, a digital signal processor for digitizing and digitally processing the difference signal, and a switch controllable to short-circuit the input of the amplifier, where the digital signal processor is configured to calculate a transfer function of the analog signal processor from the digitized difference signal received in response to short-circuiting the input of the amplifier at a given time when solely the reference carrier fluid passes the measuring cell, and the digital signal processor is further configured to recover the detector signal in digitized form by deconvoluting the digitized difference signal with the transfer function.

The terms "amplifier" and "subtracting means" referred to are to be understood in a generic sense and also include, e.g., an amplifier of inverting type followed by an adder.

In accordance with the invention, the method for operating the thermal conductivity detector comprises: passing a sample fluid in a reference carrier fluid stream through a measuring cell and generating a detector signal via a thermal conductivity detector element, processing the detector signal by an analog signal processor including amplifying the detector signal, providing a running average of the amplified detector signal by low-pass filtering, and generating a difference signal from the amplified detector signal and the running average, and digitizing and digitally processing the difference signal, where the method further comprises, as an initial step, short-circuiting the input of the amplifier, and calculating a transfer function of the analog signal processor from the digitized difference signal received in response to short-circuiting the input of the amplifier at a given time when solely the reference carrier fluid passes the measuring cell, where digitally processing the difference signal includes recovering the detector signal in digitized form by deconvoluting the digitized difference signal with the transfer function.

The term "running average" should not be understood in the usually narrow sense of "moving average" but in the broader sense of a DC component or baseline of the amplified detector signal. In accordance with the invention, the running average or DC component or baseline is removed from the amplified detector signal to obtain a difference signal that is only representative of the sample and therefore can be effectively digitized with a high level of resolution. The analog low-pass filter, however, does not only remove the DC component or baseline but also affects higher frequency signal portions representing the sample. In order to reduce or correct this effect, the detector signal is recovered or restored in digitized form by deconvoluting (unfolding) the digitized difference signal with the transfer function of the analog signal processor of the thermal conductivity detector. The transfer function is determined in advance by applying a step function or impulse function to the analog signal processor at a given time when solely the reference carrier fluid passes the measuring cell and evaluating the step or impulse response. The step or impulse function is performed by a switch for short-circuiting the input of the analog signal processing portion, i.e., the input of the amplifier, so that the signal path of the detector signal is unchanged. When the switch is open, it has no effect (including noise effects) on the thermal conductivity detector element. When the switch is closed, it shorts the detector element and the amplifier responds with a change in output.

When used in a process gas chromatograph, the switch is closed at the start of each or every n-th chromatographic cycle for a short time while solely the reference carrier gas flows through the measuring cell. The timing of the switch may be controlled by the digital signal processor of the thermal conductivity detector, which digital signal processor portion in turn may be controlled by a higher-level control system of a gas chromatograph.

As the thermal conductivity detector in accordance with the invention shows its advantages in particular in gas chromatography, a gas chromatograph comprising at least one thermal conductivity detector as described so far is a further subject of the invention.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

The invention will now be described by way of example and with reference to the accompanying drawing, in which.

DETAILED DESCRIPTION OF THE EXEMPLARY EMBODIMENTS

Figure 1:
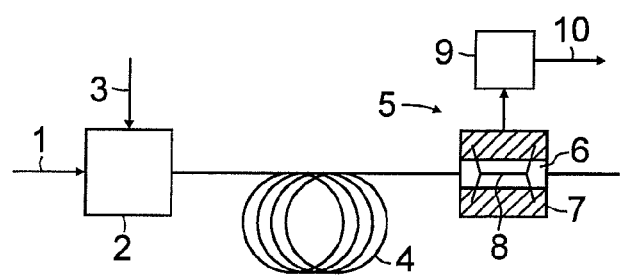
FIG. 1 is a simplified schematic block diagram of an exemplary gas chromatograph having a thermal conductivity detector in accordance with the invention.

FIG. 1 shows a gas chromatograph in which a carrier gas 1 is delivered to an injector 2, loaded there with a sample of a gas mixture 3 to be analyzed and subsequently introduced into a separation device 4 such as a single separation column or a complete system of separation columns. The separated components or substances of the gas mixture emerging successively from the separation device 4 travel to a thermal conductivity detector 5. Here, the separated gas components are conveyed in a measurement channel 6 of a measuring cell 7 past a detector element 8 such as an electrically heated heating filament. Depending on the thermal conductivity of the gas components respectively flowing past in comparison with that of the carrier gas, more or less heat is transferred from the heating filament 8 to the channel wall so that the heating filament 8 is correspondingly cooled or heated. As a result, the electrical resistance of the heating filament 8 changes, where the change is detected in an evaluation device 9 of the detector 5. To this end, the heating filament 8 may be arranged in a measurement bridge in a manner known per se (not shown). The evaluation device 9 provides an output 10 that indicates the presence and amount of the gas components passing the heating filament 7.

Figure 2:
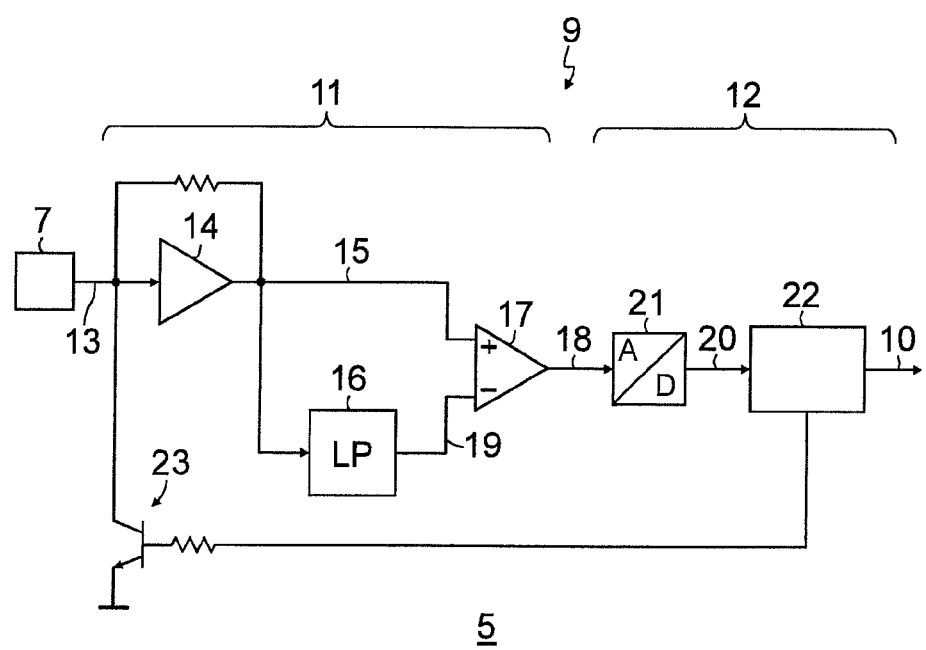
FIG. 2 is an exemplary embodiment of the thermal conductivity detector according to the invention.

FIG. 2 shows in a simplified schematic diagram an exemplary embodiment of the thermal conductivity detector 5 including the measuring cell 7 and the evaluation device 9, which consists of an analog signal processing portion 11 and a digital signal processing portion 12. The detector element 8 (see FIG. 1) provides a detector signal 13 that is conditioned and amplified by an input-side amplifier 14 of the analog signal processing portion 11. The amplified detector signal 15 is fed once directly and once via a low-pass filter 16 to a subtractor 17, which is here in the form of a differential amplifier. The subtractor 17 generates a difference signal 18 from the amplified detector signal 15 and its running average 19 formed by the low-pass filter 16. The analog difference signal 18 is then converted to a digital signal 20 by an analog-to-digital converter 21 and passed to a digital signal processor 22 for further processing and generating the output 10.

A switch 23, here in the form of an NPN transistor, is arranged between the input of the amplifier 14 and ground. The switch 23 is controlled by the digital signal processor 22 to close and thus short-circuit the input of the amplifier 14 at the start of each or every n-th chromatographic cycle for a short time while solely the reference carrier gas 1 flows through the measuring cell 7. The amplifier 14 responds with a rapid change in its output, effectively being a step function. The analog signal processing portion 11 responds by what is the convolution of the step function and the impulse response of the analog signal processing portion 11 itself. Thus, the transfer function f(n) of the low-pass filter 16 and the transfer function 1−f(n) of the combined low-pass filter 16 and subtractor 17 can be calculated from the digitized difference signal 20 received by the digital signal processor 22 in response to the step function. This allows for characterizing and, if necessary, adapting the low-pass filter 16.

When a chromatographic cycle starts and the sample in the carrier gas stream passes through the measuring cell 7, the switch 23 is open and has no effect on the detector element 8 and the subsequent processing electronics. As the low-pass filter 16 not only removes a DC component from the amplified detector signal 15 but also affects higher frequency signal portions which represent the sample, the difference signal 18 will be distorted correspondingly. The digital signal processor 22 therefore restores the detector signal in digitized form by deconvoluting the digitized difference signal 20 with the transfer function 1−f(n) of the analog signal processing portion 11.

The operating sequence of the thermal conductivity detector 5 may be as follows:

1. Wait until a previous sample is cleared from the separation device 4 and the tubing to the measuring cell 7, such that only carrier gas 1 is flowing.
2. Apply step function (close switch 23).
3. Acquire transfer function of the analog signal processor 11 from the step response.
4. Remove step function (open switch 23).
5. Allow system to settle after removal of step function.
6. Start chromatographic cycle.

7. End of chromatographic cycle.

8. Restore detector signal by deconvoluting the received difference signal 20 with the transfer function of the analog signal processor 11.

9. Decide if low-pass filter 16 needs to be re-characterized; if so return to step 1.

10. Else: Go back to step 6.

One significant advantage of the invention is that the operating sequence of the thermal conductivity detector and thus of the gas chromatograph is closer to being a continuous process because the low-pass filter time constant needs to be set only at some multiple of the widest chromatographic peak of interest. This keeps from having a low pass filter that requires many seconds or even minutes to settle and be ready for a measurement. DC drift of the low-pass filter 16 is also less important because this would be calibrated out in the transfer function.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A thermal conductivity detector comprising:
   a measuring cell containing at least one thermal conductivity detector element and providing a detector signal and being passed through by a sample fluid in a reference carrier fluid stream;
   an analog signal processor including an amplifier for amplifying the detector signal, a low-pass filter for providing a running average of the amplified detector signal, and a subtractor for generating a difference signal from the amplified detector signal and the running average;
   a digital signal processor for digitizing and digitally processing the difference signal, said digital signal processor deconvoluting the digitized difference signal with a transfer function to recover the amplified detector signal in digitized form; and
   a switch controllable to short-circuit an input of the amplifier;
   wherein the digital signal processor is configured to calculate the transfer function of the analog signal processor from the digitized difference signal received in response to short-circuiting the input of the amplifier at a given time when solely the reference carrier fluid passes the measuring cell such that the thermal conductivity detector is operated in a substantially continuous manner to increase an operating speed of a gas chromatograph.

2. A gas chromatograph comprising at least one thermal conductivity detector of claim 1.

3. A method for operating a thermal conductivity detector comprising:
   passing a sample fluid in a reference carrier fluid stream through a measuring cell and generating a detector signal via a thermal conductivity detector;
   processing the detector signal in an analog signal processor including amplifying the detector signal, providing a running average of the amplified detector signal by low-pass filtering, and generating a difference signal from the amplified detector signal and the running average; and
   digitizing and digitally processing the difference signal comprising deconvoluting the digitized difference signal with a transfer function to recover the detector signal in digitized form;
   the method further comprising, as an initial step, short-circuiting an input of the amplifier at a given time when solely the reference carrier fluid passes the measuring cell and calculating the transfer function of the analog signal processor from the digitized difference signal received in response to short-circuiting the input of the amplifier such that the thermal conductivity detector is operated in a substantially continuous manner to increase an operating speed of a gas chromatograph.

* * * * *